(12) United States Patent
Meyyappan (10) Patent No.: US 9,182,394 B1
(45) Date of Patent: Nov. 10, 2015

(54) FABRICATION OF NANOPIPETTE ARRAYS FOR BIOSENSING

(75) Inventor: Meyya Meyyappan, San Jose, CA (US)

(73) Assignee: The United States of America as Represented by the Administrator of the National Aeronautics & Space Administration (NASA), Washington, DC (US)

( * ) Notice: Subject to any disclaimer, the term of this patent is extended or adjusted under 35 U.S.C. 154(b) by 839 days.

(21) Appl. No.: 13/480,917

(22) Filed: May 25, 2012

(51) Int. Cl.
  *G01N 33/566* (2006.01)
  *G01N 33/543* (2006.01)

(52) U.S. Cl.
  CPC ................ *G01N 33/54386* (2013.01)

(58) Field of Classification Search
  None
  See application file for complete search history.

(56) References Cited

U.S. PATENT DOCUMENTS

| | | | | |
|---|---|---|---|---|
| 6,045,677 | A * | 4/2000 | Beetz et al. | 205/50 |
| 7,939,734 | B1 | 5/2011 | Li et al. | |
| 2010/0304204 | A1 * | 12/2010 | Routkevitch et al. | 429/122 |
| 2011/0181169 | A1 * | 7/2011 | Eden et al. | 313/231.31 |
| 2013/0071297 | A1 * | 3/2013 | Eden et al. | 422/186.07 |
| 2014/0023956 | A1 * | 1/2014 | Moghaddam et al. | 429/491 |

OTHER PUBLICATIONS

J. Li et al, "Carbon Nanotube Nanoelectrode Array for Ultrasensitive DNA Detection," Nano Letters, Mar. 22, 2003, 597-602, 3, American Chemical Society.
M. Karhanek et al, "Single DNA Molecule Detection Using Nanopipettes and Nanoparticles," Nano Letters, Jan. 5, 2005, 403-407, 5-2, American Chemical Society.
S. Schafer et al, Time-dependent fObservation of Individual Cellular Binding Events to Field-effect Transistors, Biosensors and Bioelectronics, Jul. 12, 2008, 1201-1208, 24, Esseview B.V.
M. Meyyappan, et al., Inorganic Nanowires: Applications, Properties and Characterization, 2009, Chapter 3, 17-58, CRC Press, Boca Raton, FL.
M. Meyyappan, et al., Inorganic Nanowires: Applications, Properties and Characterization, 2009, Chapter 14, 313-347, CRC Press, Boca Raton, FL.
Periyakaruppan, et al., Detection of Ricin Using a Carbon Nanofiber Based Biosensor, Biosensors and Bioelectronics, Jul. 31, 2011, 428-433, 28, Elsevier B.V.

* cited by examiner

*Primary Examiner* — Ann Lam
(74) *Attorney, Agent, or Firm* — John F. Schipper; Robert M. Padilla (57) ABSTRACT

Method for providing a nanopipette array for biosensing applications. A thin substrate of anodizable metal ("AN-metal," such as Al, Mg, Zn, Ti, Ta and/or Nb) is anodized at temperature T=20-200° C., chemical bath pH=4-6 and electrical potential 1-300 Volts, to produce an array of anodized nanopipette channels, having diameters 10-50 nm, with oxidized channel surfaces of thickness 5-20 nm. A portion of exposed non-oxidized AN-metal between adjacent nanopipette channels, of length 1-5 μm, is etched away, exposing inner and outer surfaces of a nanopipette channel. A probe molecule, is deposited on one or both surfaces to provide biosensing capability for K($\geq$1) target molecules. Target molecule presence, in an above-threshold concentration, in a fluid passed through or adjacent to a nanopipette channel, produces characteristic detection signals associated with the probe molecule site.

19 Claims, 4 Drawing Sheets

FABRICATION OF NANOPIPETTE ARRAYS FOR BIOSENSING

ORIGIN OF THE INVENTION

This invention was made by one or more employees of the U.S. government. The U.S. government has the right to make, use and/or sell the invention described herein without payment of compensation, including but not limited to payment of royalties.

FIELD OF THE INVENTION

This invention relates to formation of an array of nanopipettes with diameters 10-50 nm in a variety of metal-like materials, as nanopipettes for reacting with flows of selected molecules for biosensing.

BACKGROUND OF THE INVENTION

Development of biosensors is an active field, with applications in lab-on-a-chip, diagnostics of infectious diseases, cancer diagnostics, environment monitoring, biodetection and other fields. One strategy used for selective identification of a biological target is to preselect a probe that has a unique affinity for the target or that can uniquely interact with or hybridize the target, using a "lock and key" approach. In this approach, one needs a platform to support the probe and a recognition element that can sense presence of the desired interaction between the probe and the target. The interaction result can manifest itself optically (using dyes, quantum dots for example) or electrically. The platform design and configuration may vary, depending on whether optical or electrical interaction is used. Electrical readout biosensors have gained much attention because, in principle, they can be made more compact than optical technologies.

Advances in microfabrication and related technologies have aided development of electrical readout based biosensors. One popular approach is a bio-field effect transistor (Bio-FET), wherein a probe molecule is functionalized in the gate region of a three-terminal transistor [Schafer et al, "Time-dependent observation of individual cellular binding events to field-effect transistors," Biosensors and Bioelectronics. Vol 24 (2009) pp. 1201-1208]. When the probe-target hybridization takes place, a shift occurs in the threshold voltage of the current-voltage curve from the corresponding curve before hybridization. Wafer scale fabrication of Bio-FETs can assure reasonable unit cost for each sensor.

Figure 1:
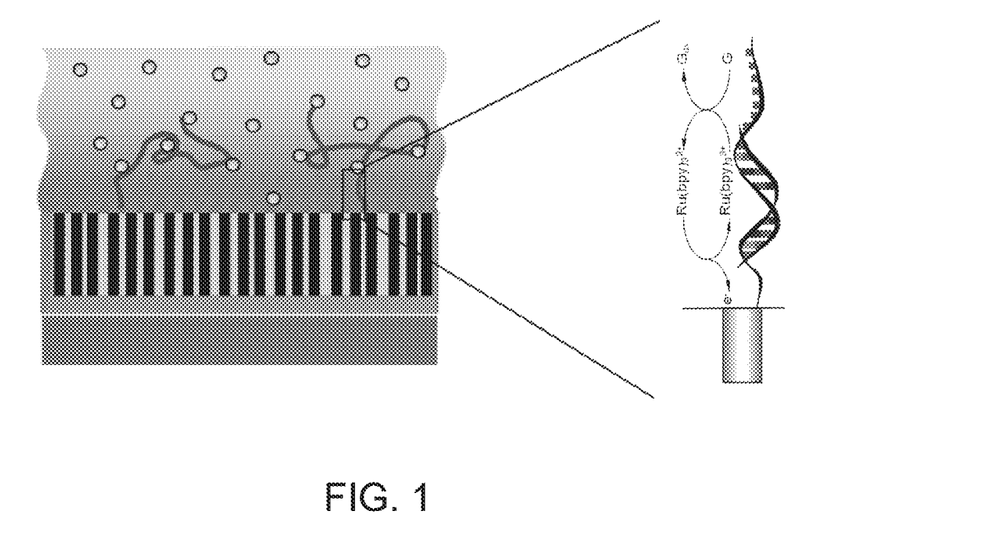
FIG. 1 illustrates an array of carbon nanofibers in the prior art, with a probe molecule attached to a tip of each nanofiber for hybridization.

Another competing electrical readout technology relies upon use of an electrode instead of a transistor. In this approach, the electrode tip has an attached probe, and when hybridization with the target occurs, the generated signal will be transmitted by the electrode to a measurement circuit. A previous NASA Ames innovation [Jun Li et al, "Carbon Nanotube Nanoelectrode Array for Ultrasensitive DNA Detection," Nano Letters, vol. 3 (2003) pp. 597-602] involves a nanoelectrode array consisting of an array of carbon nanofibers as individual nanoelectrodes, as illustrated in FIG. 1. Each nanofiber is a solid nanocylinder having a probe attached to it, and the array size, chip size and wafer size are controlled.

Other approaches have used various inorganic nanowires, such as silicon or oxide nanowires instead of carbon nanofibers; these nanowires are also solid cylinders [M. Meyyappan and M. Sunkara, "Inorganic Nanowires: Applications, Properties and Characterization," Chap. 14, CRC Press, Baton Rouge, Fla., (2009)]. Others have used gold quantum dots, which are small solid spheres. The probe attachment is done on the tip of the cylinder or outer surface of the sphere for each of these approaches.

Figure 2:
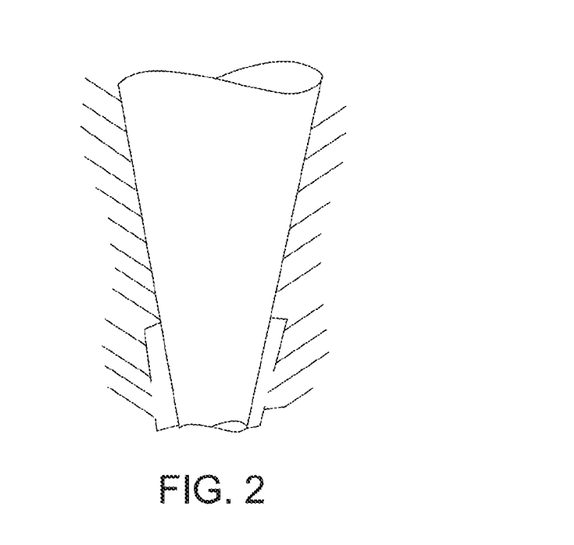
FIG. 2 illustrates a nanopipette tapered end that may be used as a biosensor.

A more recent approach involves use of a nanopipette, which is a tiny hollow tube with probe molecule attached at a tapered end on the external surface. FIG. 2 illustrates a nanopipette configuration. M. Karhanek et al, "Single DNA Molecule Detection Using Nanopipettes and Nanoparticles," Nano Letters, vol. 3 (2003) pp. 403-407] report use a quartz capillary which is drawn into a tiny pipette using a laser puller, with an inner diameter of about 50 nm. Probe functionalities chosen for a specified target are attached to the outside surface of the nanopipette tip. This approach provides a competitive technique for biosensing, when compared with the Bio-FET or any of the nanoelectrode approaches discussed above. One problem encountered is that pulling a pipette out of a glass capillary using a laser puller (or any other pulling approach) yields one pipette at a time. A feasible biosensing technology will require an array of nanopipettes, by analogy with the competing technologies of Bio-FETs arrays or nanoelectrodes arrays.

A useful approach would permit would formation of an array of nanopipettes with controllable diameters, densities and/or lengths.

SUMMARY OF THE INVENTION

The present invention provides an array of nanopipette channels, formed and controlled in a metal-like material that supports anodization. The invention also permits selective first and second functionalizations. (different or the same) of first and second channel surfaces, respectively, so that different reactions of a multi-component fluid flowing in the channels can be evaluated simultaneously.

The materials that support anodization include aluminum, magnesium, zinc, titanium, tantalum and niobium, referred to herein as "AN-metals." The relevant, controllable anodization parameters include applied electrical potential, current density, electrolyte concentration, solution pH, solution temperature and anodization time. The channel parameters affected include pore diameter, pore density (or spacing) and maximum pore length (channel length). An anodization process is initially applied to provide a plurality of adjacent nanopipette channels having inner diameters d in a selected range, such as 10-50 nanometers (nm). The center-to-center spacing s of the nanopipette central axes preferably lies in a range $f1 \cdot d \leq s \leq f2 \cdot d$, with $f1 \approx 1.5$ and $f2 = 2-10^3$, and the channel length L is arbitrary. A selected length L1 (less than L) of exposed AN-metal, lying between two or more adjacent nanopipette channels is partially removed (e.g., by etching) and an exposed surface is functionalized with one or more selected probe molecules that will interact with a selected chemical or biological substance to which the nanopipette array is exposed. The nanopipette array can be applied in biosensing, biomedicine, life detection, environmental sensing and security, to sense presence of a specified component(s), by production of a characteristic signal associated with the functionalized site in the presence of the specified component. Differing concentrations of the same specified component can also be estimated.

A first application of the invention involves detection of presence of a biothreat gas or fluid, such as the nerve agent Ricin (made from castor bean seeds). A second application involves detection of troponin, a protein that is important in diagnosis of a heart attack. These applications are discussed in the following description.

DESCRIPTION OF BEST MODES OF THE INVENTION

Several metals, including aluminum, magnesium, zinc, titanium, tantalum and niobium, (referred to collectively herein as "AN-metals") will spontaneously form a thin oxide covering (typically 200-500 nm thickness for Al), when exposed to a gas containing oxygen. Anodization is an electrostatic process that can be used to increase the natural oxide thickness, provide a surface coloring associated with this thickness, and provide a plurality of pores in the oxide covering. This oxidization process does not work for most other metals and semi-metals, such as carbon and iron, because the exposed covering for these substances exfoliate when oxidized. As a result of the oxidization of an AN-metal, the crystal structure of this substance is changed near the surface. Wear resistance is sometimes improved, but the resulting substance may become more brittle. The anode layer itself is usually electrically and thermally non-conductive and can serve as a dielectric. However, the thermal expansion coefficient of the aluminum oxide is substantially different from the corresponding coefficient of pure aluminum so that the anozdized layer may crack from thermal stress differences for temperatures above 80° C.

Summary of an Anodization Process.

Anodization is one of several processes for providing a template to guide or control one-dimensional growth or deposition of a material. In one approach, a thin foil or membrane of an AN-metal as anode, including but not limited to Al, is placed in a chemical bath (e.g., chromic, sulfuric, phorphoric, nitric, boric or organic acid, etc.) with a pH in a range about 4-6, maintained at a solution temperature in a range about $T=20-200°$ C., preferably $40°$ C.$\leq T \leq 80°$ C. with a selected non-AN-metal (e.g., Pb and/or Fe), spaced apart and acting as a cathode. Electrical current with density up to about 10 Amps/cm$^2$ is introduced in the bath. An oxide forms on an exposed surface of the AN-metal, and a portion of this oxide thickness is removed by the acid bath. Where the chemical bath has a pH less than 5, pores will develop in the AN-metal. Where the pH is greater than 5, a non-porous oxide barrier of estimated thickness 5-20 nm often forms on an exposed surface of the AN-metal.

Use of relatively low electrical potential values and current densities and of relatively low temperatures ($T<60°$ C.) will more likely produce non-porous oxide barriers. The associated electrical field will have a higher magnitude in regions of thinner oxide so that formation of pores will usually begin in these regions and will propagate toward regions with thicker oxide layers. Pore diameter and pore spacing are reasonably uniform and tend to increase linearly with the applied electrical potential, with proportionality constants on the order of 1-3 nm/(Volt difference). The relevant anodization parameters include applied electrical potential, current density, electrolyte concentration, solution pH, solution temperature and anodization time. The channel parameters affected or controlled include pore diameter, pore density (or spacing) and maximum pore length (channel length). Where a one-step anodization process is used, the pore density is high ($\approx 10^2$-$10^{10}$ pores/cm$^2$), but the pore length may be limited. A multi-step anodization process will provide larger pore lengths and better control of pore diameter.

Anodization as Used in the Invention.

An anodized aluminum oxide layer (AAO layer in FIG. 3) is formed by passing a dc electrical current through an electrolyte solution (pH about 4-6) between a cathode e.g., Pb and/or Fe) and the AN-metal (e.g., Al), serving as anode. The current used is often in a range 0.3-3 Amps/cm$^2$, with an electric potential of about 1-300 Volts (dc), more preferably, 10-30 Volts. Solution temperatures in a range $T \approx 20-200°$ C. may be used. Anodization is often performed in an acid chemical bath solution (chromic, sulfuric, organic, phorphoric, boric or nitric acid, etc., with pH$\approx$4-6), which can be chosen to slowly dissolve a portion of the oxide coating and to form nanopipette channels with diameters 10-150 nanometers (nm), that are partly controllable by choice of solution pH and current density. The film thickness can vary in a range 0.5-150 µm (microns). The process will provide an array of nanopipettes, partly or wholly filled with oxide (e.g., Al$_2$O$_3$) and with central axes approximately perpendicular to a plane of the substrate.

Anodized Mg may be made with oxide thicknesses of 5-25 µm or larger. Anodized Zn can be made with larger oxide thicknesses, 5-25 µm or more, using electrical potentials up to about 200 Volts. Anodized Ti can be made with an oxidized thickness in a range 50-300 nm. Anodized Ta can be made with oxide thicknesses of the order of 1-2 nm, dependent upon the (small) voltages used. Anodized Nb oxide thicknesses will depend upon the voltages applied.

Figure 3:
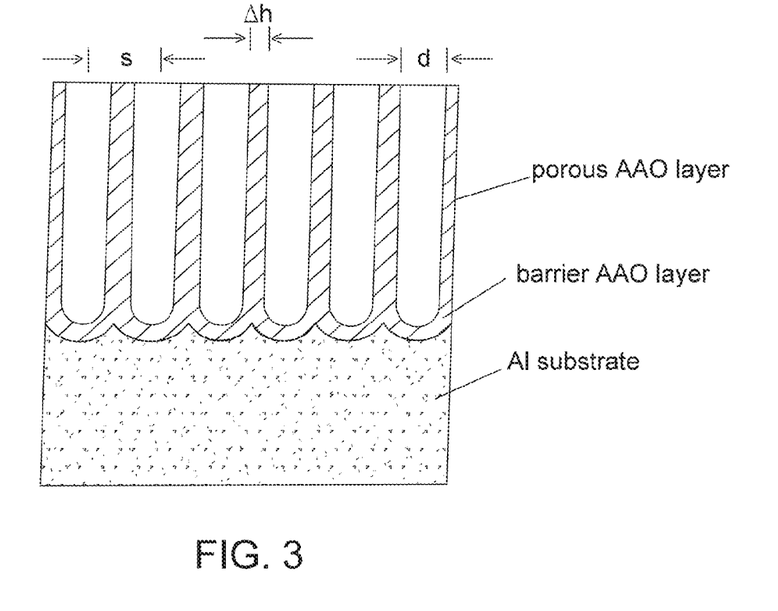
FIG. 3 schematically illustrates a sectional view of a nanopipette array at an intermediate stage of the procedure shown in FIG. 5.

FIG. 3 schematically illustrates a sectional view of a nanopipette array at an intermediate stage of procedure for forming the array. Each nanopipette in the array is defined by a porous barrier (thickness h) of oxidized material, with a diameter about d=10-50 nm and a selected center-to-center spacing s=1.5 d-2,000 d. The quantities h, d and s will each have a characteristic range of values.

The most common nanoporous material is anodized alumina membrane or template, as illustrated in FIG. 3, which shows an intermediate array of nanopipettes, with diameter d nominally 10-50 nm. Application of biosensing can be done by at least two approaches. A first approach of the invention attaches probe molecules to inner surfaces of the nanopipettes. The entire length of the nanopipettes need not be used; an upper channel portion of length 1-5 µm will suffice. This would allow formation of the nanopipette array in FIG. 4 to be used as shown.

A second approach of the invention utilizes an external surface and, optionally, an internal surface, and requires the exposure of an upper channel portion of these surfaces, of length D1 about 1-5 µm. Exposure of the nanopipettes external surface can be done by selective etching of the AN-metal by phosphoric acid. Operation at $T=60°$ C. is appropriate for etching the template, depending upon the metal(s) used. The etch time depends on the length of the channel to be removed (e.g., 1-5 µm). After sufficient alumina is removed, nanopipettes extend 1-5 µm from the template exposing the external surface for functionalization.

The starting material can be aluminum film or another AN-metal or a thin sheet of AN-metal. The film is annealed at 500° C. for 3 hours. Polishing is done next to reduce surface roughness and obtain a mirror smooth finish. The finished film is placed in an acid bath (sulfuric acid, phosphoric acid or another acid with pH less than 6, and preferably less than 5) and a direct current (dc) is applied. The acid bath needs to be stirred to release the hydrogen bubbles formed. Pore diameter and pore spacing are controlled by choices of applied potential, type of acid, acid pH and the bath temperature.

In addition to anodized alumina template, other templates can also be used as nanopipette array, for example zeolite pores, and even pores in DNA, but these are much harder to use. Pores can also be etched, using focused ion beam etching or other plasma etching techniques, on thin silicon nitride or other membranes.

Figure 4:
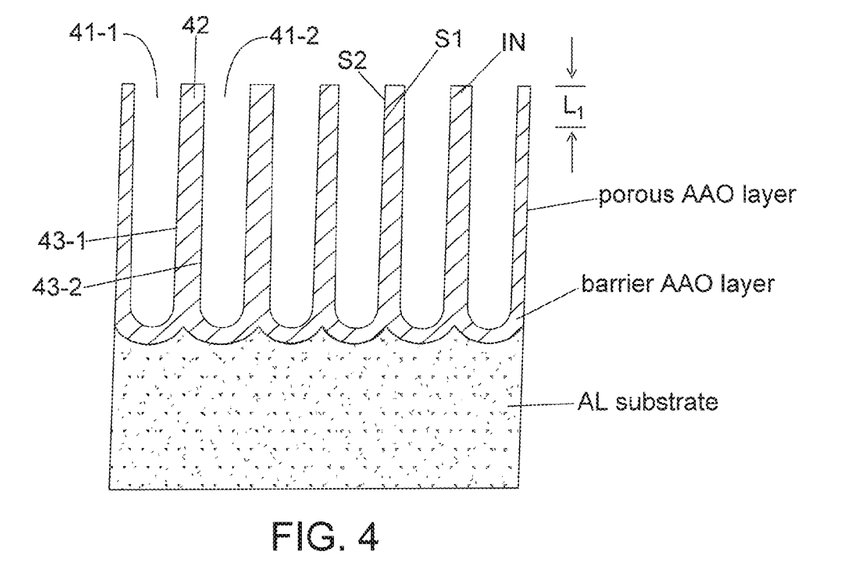
FIG. 4 schematically illustrates a sectional view of a nanopipette array that can be formed after the stage shown in FIG. 3 is completed.

FIG. 4 schematically illustrates a sectional view of a nanopipette array that results after the procedure is completed: a small length L1 of the interior IN of the porous barrier layer has been etched away, leaving a thinner exposed region, having an inner surface S1 and an outer surface S2. Probe molecules can be attached to an exposed surface (S1 and/or S2) after etching has occurred, with the particular biosensing probe molecule being selected according to the application. For example, the probe molecule may be selected for binding with an undesirable target molecule, such as $E.\ coli$, H1N1, $salmonella$, botulism, or with a particular poison, toxin or nerve agent. The target molecule may attach to, and allow subsequent detection of, a characteristic electrical signal that is otherwise not detected.

The anodized material produced in FIG. 3 is shown in greater detail in FIG. 4, where two adjacent nanopipette channels, 41-1 and 41-2, are separated by at least one thin, oxidized layer 42, and by AN-metal layers, 43-1 and 43-2. One goal here is to etch or otherwise remove a selected length L1 of the AN-metal layer 43-(1,2) and to leave the thin, oxidized layer 42 with one or two surfaces that can be functionalized or provided with selected probe molecules. Choice of the etchant will depend the AN-metal layer 43-(1,2) that is to be removed. Pure aluminum and pure magnesium (non-oxidized) may be removed by HCl or by a mixture of $H_3PO_4$ and $HNO_3$. Other metals (non-oxidized), such as Zn, Ti and Ta may be removed by selected mixtures of $H_3PO_4$, $NH_4OH$, NaOH and/or $H_2O_2$. Some of these etchants are anisotropic, rather than being isotropic, which can be helpful in minimizing removal of the oxidized layers 42. One should avoid use of etchants such as BHF or HF, which may selectively target oxides of an AN-metal, such as ZnO, in the oxidized layers 42. Ideally, the etchant will remove the non-oxidized AN-metal and leave most of the oxidized AN-metal as thin layers, 43-1 and 43-2, between two adjacent nanopipette channels, 41-1 and 41-2.

After etching is completed, a first probe molecule can be deposited on the exposed outer surfaces of the oxidized layers; and/or a second probe molecule can be deposited on the exposed inner surfaces. These probe molecules are chosen to react selectively with a specified component of a gas or other fluid that flows through the resulting nanopipette channels, 41-1 and/or 41-2.

Figure 5A:
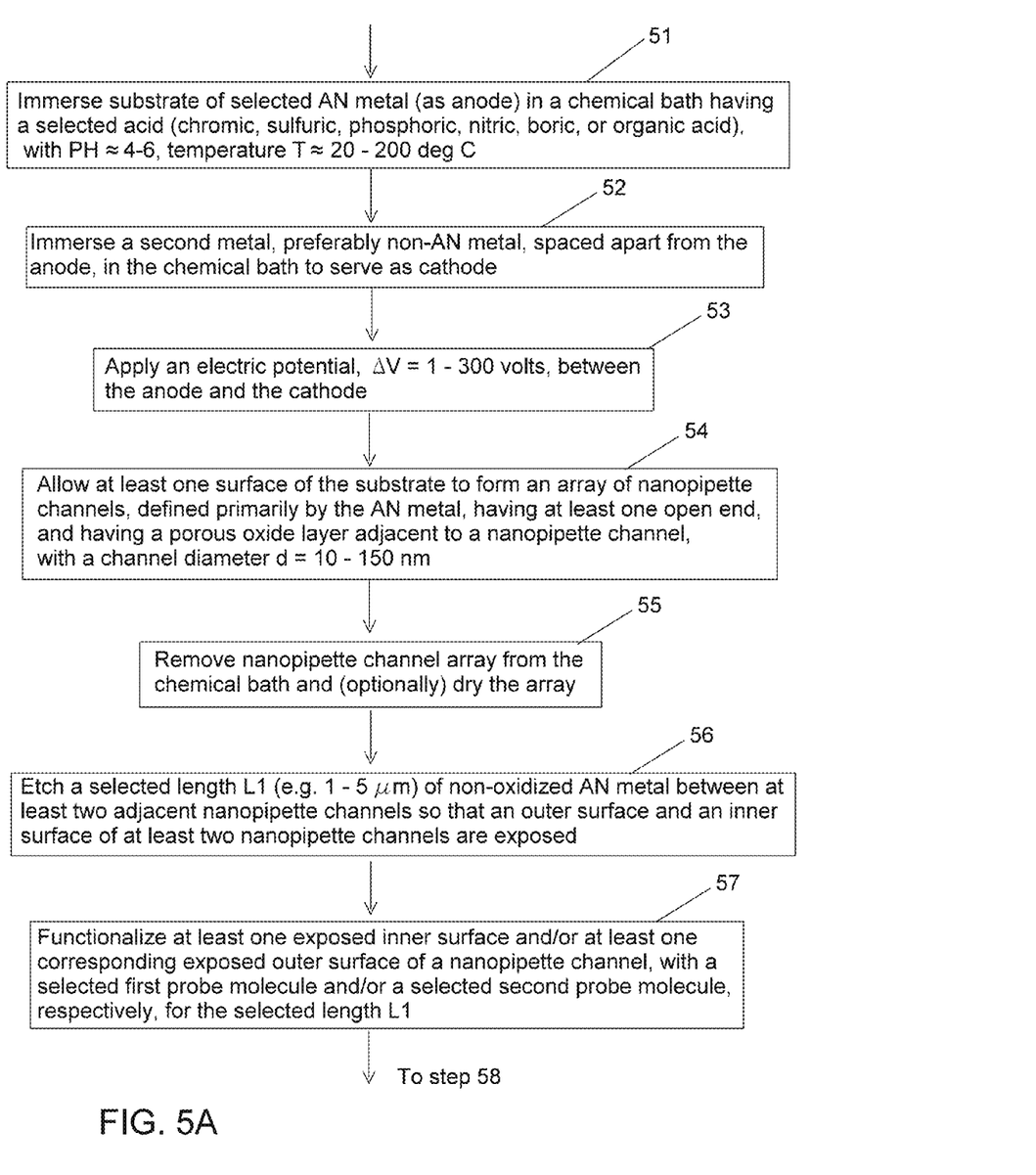
FIG. 5 is a flow chart of an embodiment of a procedure for forming a nanopipette array according to an embodiment of the invention.
Figure 5B:
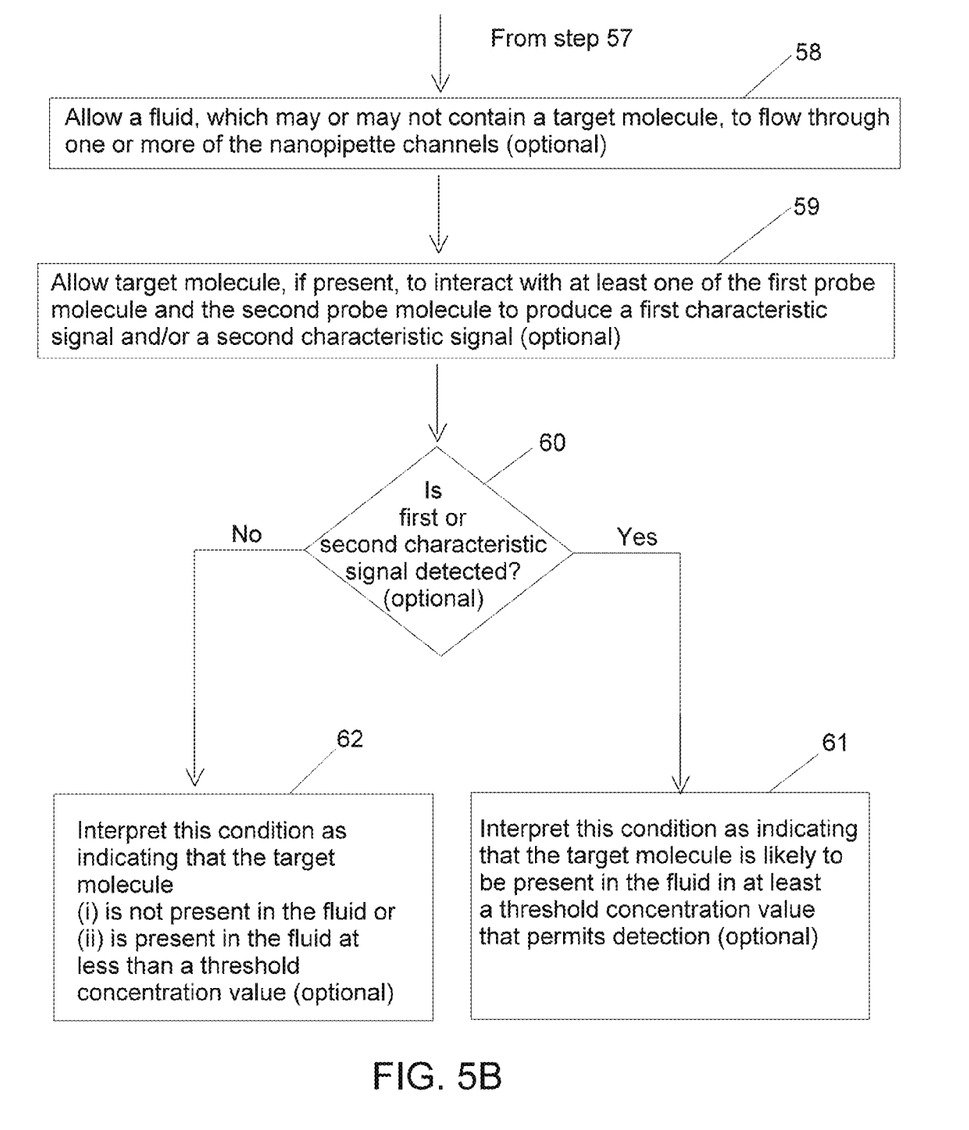

FIG. 5 is a flow chart of a procedure that can be used to practice the invention and apply it to sensing presence of a target molecule. In step 51, a substrate of a selected AN-metal is immersed in a chemical bath, including a selected acid (e.g., chromic, sulfuric, phosphoric, nitric, boric or organic acid), having a pH in a selected range, such as 4-6, and having a solution temperature T in a selected range, such as 20° C.$\leq$T$\leq$200° C., preferably 40° C.$\leq$T$\leq$80° C. The AN-metal may be Al, Mg, Zn, Ti, Ta, Nb or another metal that responds appropriately to anodization and will serve as an anode. In step 52, a non-AN metal, such as Pb or Fe, is immersed in the chemical bath to serve as a cathode, spaced apart from the anode.

In step 53, an electrical potential having a value in a range 1-300 Volts dc, preferably 10-30 Volts dc, is applied between the cathode and the anode, with a chemical bath pH of about 4-6. In step 54, at least one surface of the substrate is allowed or caused to form an array of nanopipette channels, defined primarily by AN-metal, with each such channel having at least one open end and having a porous oxide layer adjacent to and defining the nanopipette channel. As noted above, the average nanopipette channel diameters in the oxidized AN-metal will tend to increase with increasing voltage difference. Here, the desired average nanopipette channel inner diameter d is in a range of about 10-150 nm, and more preferably in a range 10-50 nm.

In step 55, the nanopipette channel array is removed from the chemical bath and optionally dried. At this point, the array of nanopipette channels resembles the array shown in FIG. 3, which includes a plurality of nanopipettes with most diameters in a selected diameter range (e.g., d=10-50 nm), with a channel density in a selected density range (e.g., $10^2$-$10^{10}$/$cm^2$), and in a range of channel lengths.

In step 56, a selected length, such as L1$\approx$1-5 μm, of non-oxidized AN-metal between two or more adjacent nanopipette channels is etched or otherwise removed, as illustrated in FIG. 4, so that an outer surface and an inner surface of at least two nanopipette channels are exposed, as discussed in connection with FIG. 4. In step 57, at least one of the exposed inner surfaces and/or at least one of the corresponding exposed outer surfaces of a nanopipette channel is functionalized with a selected first probe molecule and/or with a selected second probe molecule, respectively, for the selected length L1. One result of this process is an array of nanopipettes in which at least one (open) end of each nanopipette is functionalized on one or two selected surfaces.

In a first version of a biosensing application, a first probe molecule is provided on an exposed inner surface of a nanopipette array channel and a second probe molecule (optionally the same as, or different from, the first probe molecule) is provided on an exposed outer surface of the nanopipette array channel. In step 58 (optional), a fluid, which may or may not include a target molecule that binds with the first probe molecule to thereby allow detection of a first characteristic signal, and/or that binds with the second probe molecule to thereby allow detection of a second characteristic signal, is allowed or caused to flow through one or more of the nanopipette array channels. In step 59 (optional), the target molecule, if present in the fluid, is allowed to interact with at least one of the first probe molecule and/or the second probe molecule to produce a first characteristic signal and/or a second characteristic signal, respectively. In step 60 (optional), the system determines whether the first characteristic signal and/or the second characteristic signal is detected, for example, by interrogation of a site including the first probe molecule, and/or by interrogation of a site including the second probe molecule. In step 61 (optional), when at least one of the first characteristic signal and the second characteristic signal is detected, the system interprets this condition as indicating that the target molecule is likely to be present in the fluid in at least a threshold concentration value that permits detection. In step 62 (optional), when neither the first characteristic signal nor the second characteristic signal is detected, the system interprets this condition as indicating that (i) the target molecule is not present in the fluid or (ii) the target molecule is present in the fluid, but in a concentration that is less than a threshold concentration value that will produce the characteristic signal.

In a second version of a biosensing application, only one of the exposed inner surface and the exposed outer surface of a nanopipette array is provided with a probe molecule. The following steps in FIG. 5 are modified.

Step 56: Only one of the inner and outer surfaces is exposed.

Step 57: The exposed surface is functionalized with a probe molecule

Step 60: Presence of (only) a first characteristic signal is determined

Step 61: When presence of the first characteristic signal is detected, the system interprets this as indicating that the target molecule is likely present in at least a threshold concentration value C(thr).

Step 62: When presence of the first characteristic signal is not detected, the system interprets this as indicating that (i) the target molecule is not present or (ii) that target molecule is present in less than the threshold concentration value C(thr).

Where the exposed inner and outer surfaces are to be functionalized with different probe molecules and a large number N of nanopipette channels (N≥2) is provided, at least four alternative approaches are available. In a first alternative, the inner and outer exposed surfaces ("sites") are functionalized with the same probe molecule, with each of the 2N sites having an independent readout mechanism. In this alternative, an observed number N1 of the 2N sites will provide a detectable signal, and each such site is assigned a probability p (as yet unknown) that the target molecule concentration associated with that channel has an above-threshold value. Adopting a binomial distribution with a probability p that the concentration is at or above the threshold value and probability 1−p that the concentration is below the threshold value, the probability that n1 (out of 2N) sites have a detectable concentration of the target molecule is $$B(N1;2N;p) = (^{2N}_{N1}) p^{N1} (1-p)^{2N-N1} \quad (1)$$

The *mean* value for *this* distribution is $$p(\text{mean}) = (2N)p, \quad (2)$$

and this mean value equals N1 if $$p = N1/2N. \quad (3)$$

A confidence level can be chosen, with a corresponding value of probability p1^, and the system interprets the measurements as indicating that the target molecule is present if (or only if)

$$N1 \geq (2N)(p1^\wedge). \quad (4)$$

In a second alternative, the N exposed inner surfaces of the channels are functionalized with a first probe molecule and the N exposed outer surfaces are functionalized with a second probe molecule, with each of the probe molecules being chosen to detect the same target molecule. Each of the first and second probe molecules may have substantially the same threshold concentration or (optionally) may have different concentration thresholds. Where the first and second probe molecules have different concentration thresholds, C1(thr) and C2(thr) (>C1(thr)), and different characteristic detection signals, the target molecule concentration C(target) can be estimated more finely to lie in one of the three concentration regions, C(target)<C1(thr), C1(thr)≤C(target)<C2(thr), and C(target)≥C2(thr), depending upon whether (i) no detection signal occurs, (ii) only the first detection signal occurs, or (iii) the first and second detection signals occur/

It may be preferable for the first and second probe molecules to contain at least one component in common, which reacts with the target molecule and provides distinguishable first and second detection signals, respectively, at or above different (first and second) concentration values. This second alternative can be extended to detection of presence of the target molecule in any of K concentration regimes (K≥2) by use of K different probe molecules and different characteristic detection signals, preferably with at least one common component, on K mutually exclusive subsets of the exposed inner and outer surfaces.

Assume that N1(out of N) of the first probe sites detect an above-threshold concentration of the target molecule, and that N2(out of N) of the second probe sites detect an above-threshold concentration of the same target molecule. Applying the binomial distribution analysis to each of the detection numbers (N1 first probe sites and N2 second probe sites), with corresponding probability values p1^ and p2^ (not necessarily equal), the system interprets the measurements as indicating that the target molecule is present in the channels in an above-threshold concentration if $$N1 \geq (N)(p1^\wedge) \quad (5A)$$

and/or $$N2 \geq (N)(p2^\wedge). \quad (5B)$$

The user will determine the relative weights to be given to these requirements if one, but not both, of Eqs. (5A) and (5B) is satisfied.

In a third alternative, the N exposed inner surfaces of the channels are functionalized with a first probe molecule, the N exposed outer surfaces are functionalized with a second (different) probe molecule, preferably with different characteristic detection signals, and the first and second probe molecules are chosen to detect presence of distinct first and second target molecules, respectively. In this situation, the preceding binomial analysis is applied separately to the N exposed inner surface and to the N exposed outer surfaces, and Eqs. (5A) and (5B) are applied separately to estimate whether the first target molecule is present and, independently, whether the second target molecule is present. The probability values p1^ and/or p2^ can be related to corresponding threshold concentration values for signal detection purposes.

In a fourth alternative, only the N exposed inner surfaces of the channels are functionalized, OR only the N exposed outer surfaces of the channels are functionalized, and the analysis procedure is similar to that of the first alternative.

APPLICATIONS

A first application of the invention involves detection of presence of a biothreat fluid, such as the nerve agent Ricin. Ricin is a toxic glycoprotein that can be isolated from castor bean seeds and consists of two chains, A and B, connected by a disulfide bond, with a total molecular weight of about 62 kiloDaltons (kD). The B chain binds to a cell surface and acts as a transport mechanism to move the A chain into the cell interior. Inside a cell, the A chain stops protein production and leads to cell death. The $LD_{50}$ value for inhalation of Ricin is about 22 µg per 1 kg of weight, or about 1.76 mg for an adult of average size, Ingestion of Ricin (e.g., oral exposure) is less toxic, and $LD_{50}$ may be up to 20-30 mg per kg of weight. Death of the recipient occurs a few hours after ingestion or 3-5 days after inhalation. Failure of the body to make adequate protein often becomes observable only after several days delay following initial exposure. Detection of Ricin, using a carbon nanofiber-based biosensor, was reported recently by Adaikkappan, Arumagam, Meyyappan and Koehne in Biosensors and Bioelectronics, vol. 28 (2011) pp. 428-433. The sensor probe was functionalized with a Ricin aptamer (often custom designed to serve as a focused probe).

A second application involves detection in the blood of troponin, a protein that is important in diagnosis of occurrence of certain heart disorders. Troponin is a complex of three proteins, troponinC (TrC), troponinI (TrI) and troponinT (TrT), and is attached to the protein tropomysin. A three-stage process normally occurs when a relaxed muscle cell is stimulated to contract by opening of calcium channels. The calcium attaches to, and causes shape change in, troponin, to allow contraction to begin. Normally, troponin levels are low enough to be unmeasurable. Increase of the TrI level and/or TrT level in the blood often indicates presence of a heart disorder, such as myocardial infarction, cardiac confusion, defillibration, and internal or external cardioversion. However, increase of troponin levels is also found in about 40 percent of patients with other critical illnesses, such as sepsis. A first troponin level measurement is often made after a patient manifests chest or muscle pains, followed by one or two follow-on tests at six-hour intervals, together with one or more other tests that may be more specific for heart disorders. Troponin levels may remain higher 7-14 days after a heart attack. An aptamer, indicating presence of tropinin at a relatively high level, may be deposited on an inner surface and/or on an outer surface of a nanopipette channel, produced and used as described in the preceding.

Other applications of this invention include rapid response water quality monitoring, diagnostics for selected infectious diseases, and presence of trace chemicals in a sample fluid.

What is claimed is:

1. A method for providing and applying an array of M nanopipette channels (M≥2), the method comprising:
   processing a substrate comprising an AN-metal, defined herein as a metal that permits anodization of at least one surface of the substrate, to form an oxide layer and an array of a selected number M nanopipette channels (M≥2) on the at least one surface, having adjustable channel diameters in a selected channel diameter range, having adjustable channel depths in a selected channel depth range, and having channel axes oriented transverse to the at least one surface; and
   etching or otherwise removing an exposed portion of non-oxidized material between the at least two channels to an etch depth in a selected etch depth range, to provide each of the channels with an exposed inner surface and an exposed outer surface.

2. The method of claim 1, further comprising choosing said etch depth range for said non-oxidized material to be about 1-5 μm.

3. The method of claim 1, wherein said processing of said substrate of said AN-metal is implemented by a process comprising:
   immersing said substrate of said AN-metal, and immersing a non-AN-metal, spaced apart from each other, in a chemical acid bath, maintained in a selected temperature range, and in a selected pH range;
   applying an electrical potential in a selected voltage range between said AN-metal and the non-AN-metal to promote anodization at said AN-metal;
   allowing an oxide layer, having a thickness at least equal to a selected thickness, to form on said at least one surface of said substrate;
   allowing said at least one surface of said substrate to form an array of at least M nanopipette channels, with each channel having at least one open end and having an oxide layer; and
   removing said nanopipette channel array from the chemical bath, to thereby provide an array of nanopipette channels.

4. The method of claim 3, further comprising choosing said AN-metal from a group of metals consisting of Al, Mg, Zn, Ti, Ta and Nb.

5. The method of claim 3, further comprising choosing said solution temperature range to be about 20-200° C.

6. The method of claim 5, further comprising choosing said solution temperature in a range T=40-80° C.

7. The method of claim 3, further comprising choosing said voltage range to be about 1-300 Volts.

8. The method of claim 7, further comprising choosing said voltage range to be about 10-30 Volts.

9. The method of claim 3, further comprising choosing said thickness of said oxide layer to be at least about 50 nm.

10. The method of claim 3, further comprising choosing said pH of said chemical acid bath to be in a range of about 4-6.

11. The method of claim 10, further comprising choosing said chemical acid bath to include at least one of chromic acid, sulfuric acid, organic acid, phosphor acid, nitric acid and boric acid, with said pH being about 5.

12. The method of claim 3, further comprising choosing at least one of said pH, said solution temperature and said electrical field intensity so that said pores in said nanopipette array have an average pore diameter in a range of about 10-50 nm.

13. The method of claim 3, further comprising:
   choosing said AN-metal to be Al;
   choosing said temperature T to be no more than about 80° C.;
   choosing said applied electric potential in a range 10-30 Volts; and
   allowing at least one of said nanopipette channels to form with said diameter in a range of about 10-150 nm.

14. The method of claim 3, further comprising:
   choosing said AN-metal to be Mg; and
   allowing at least one of said nanopipette channels to form with channel depth in a range of about 5-25 μm.

15. The method of claim 3, further comprising:
   choosing said AN-metal to be Zn;
   choosing said electrical potential in a range 1-200 Volts; and
   allowing at least one of said nanopipette channels to form with channel depth up to about 80 μm.

16. The method of claim 3, further comprising:
   choosing said AN-metal to be Ti;
   allowing said oxide layer to form with a thickness in a range 50-300 nm; and
   allowing at least one of said nanopipette channels to form with said depth in the range of about 50-300 nm.

17. The method of claim 3, further comprising:
   choosing said AN-metal to be Ta;
   choosing said electrical potential in a range 1-30 Volts; and
   allowing at least one of said nanopipette channels to form with said depth of at least about 2 nm.

18. The method of claim 3, further comprising attaching a selected probe molecule on at least one of said exposed inner surface and said exposed outer surface of said nanopipette channels.

19. The method of claim 18, further comprising:
allowing a fluid, which may contain but need not contain, a selected target molecule that reacts with said probe molecule, to move through at least one of said nanopipette channels;
allowing said probe molecule to interact with the fluid moving through said nanopipette channels and to react with the target molecule, if the target molecule is present in the fluid;
providing or detecting a characteristic detection signal, when the target molecule is present in the fluid and reacts with said probe molecule;
when the characteristic detection signal is detected, interpreting this condition as indicating that the target molecule is likely to be present in the fluid in at least a selected target threshold concentration value; and
when the characteristic detection signal is not detected, interpreting this condition as indicating (i) that the target molecule is not present in the fluid or (ii) that the target molecule is present in the fluid in a concentration less than the target threshold concentration value.

\* \* \* \* \*